(12) United States Patent
Johnson

(10) Patent No.: US 6,765,656 B2
(45) Date of Patent: Jul. 20, 2004

(54) APPARATUS AND METHODS FOR HIGH THROUGHPUT ANALYSIS OF SAMPLES IN A TRANSLUCENT FLOWING LIQUID

(75) Inventor: Paul E. Johnson, Laramie, WY (US)

(73) Assignee: University of Wyoming, Laramie, WY (US)

( * ) Notice: Subject to any disclaimer, the term of this patent is extended or adjusted under 35 U.S.C. 154(b) by 0 days.

(21) Appl. No.: 10/323,535

(22) Filed: Dec. 18, 2002

(65) Prior Publication Data

US 2003/0137666 A1 Jul. 24, 2003

Related U.S. Application Data

(60) Provisional application No. 60/341,364, filed on Dec. 18, 2001.

(51) Int. Cl.[7] .............................................. G01N 21/00
(52) U.S. Cl. ........................................ 356/73; 356/338
(58) Field of Search .......................... 356/73, 335–343, 356/244–246, 300, 303; 250/432 R, 435–438, 573–576

(56) References Cited

U.S. PATENT DOCUMENTS 4,756,427 A * 7/1988 Gohde et al. ................ 209/3.1
5,488,469 A * 1/1996 Yamamoto et al. ........... 356/72
6,154,276 A   11/2000 Mariella, Jr. ................ 356/337
6,188,474 B1 * 2/2001 Dussault et al. ............. 356/246
6,309,886 B1  10/2001 Ambrose et al. .............. 436/63

FOREIGN PATENT DOCUMENTS

EP              0333560         9/1989

* cited by examiner

*Primary Examiner*—Michael P. Stafira
(74) *Attorney, Agent, or Firm*—Jennifer L. Bales; Macheledt Bales & Heidmiller LLP (57) ABSTRACT

Apparatus and methods for imaging multiple fluorescent sample particles in a flow channel. A flow channel defines a flow direction for samples in a flow stream and has a viewing plane perpendicular to the flow direction. A clear volume between the illuminated flow volume and the imaging optics is provided. A beam of illumination is formed as a column having a size effective to cover the viewing plane, and illuminates the flow nearly end on, or from the side. Imaging optics are arranged to view the focal plane to form an image of the multiple fluorescent sample particles in the flow stream. A camera records the image formed by the imaging optics. A computer detects and enumerates the particles in the flow.

14 Claims, 6 Drawing Sheets

Figure 6A t = -250 msec

Figure 6B t = 0 (in focus)

Figure 6C t = 250 msec

US 6,765,656 B2

APPARATUS AND METHODS FOR HIGH THROUGHPUT ANALYSIS OF SAMPLES IN A TRANSLUCENT FLOWING LIQUID

This application claims priority to the following provisional patent application and incorporates it herein by reference: No. 60/341,364, filed Dec. 18, 2001.

BACKGROUND OF THE INVENTION

1. Field of the Invention

The present invention relates to apparatus and methods for detection and enumeration of sample particles in translucent or transparent flowing liquid. In particular the present invention relates to high throughput analysis of imaged particles in a translucent flow.

2. Description of the Prior Art

Detection and enumeration of low concentrations of selected microorganisms in large volumes of fluid has a number of applications including: 1.) bioterrorism and biowarfare defense, 2.) food and water quality control, 3.) clinical detection of pathogens, and 4.) environmental monitoring. Biodetection systems developed to date usually suffer from 1.) high cost, 2.) unsatisfactory sensitivity, 3.) slowness 4.) large size and/or 5.) labor-intensive preparation steps.

Common biodetection techniques include culture-based techniques, molecular microbiological techniques (such as Polymerase Chain Reaction or PCR), direct detection using epifluorescent microscopy, conventional flow cytometry and solid phase cytometry. All of these techniques suffer drawbacks. Culture-based techniques are slow (typically taking more than 24 hours) and usually require labor intensive steps. Microbiological techniques are not strictly quantitative and are limited by interference from background material. PCR, in particular, doesn't differentiate between live and dead cells. Direct detection of single cells without the requirement for growth is desirable, as it is more rapid. In addition, detection is quantitative, as the number of cells is directly determined.

A conventional technique for direct enumeration of microorganisms in water is filtration and microscopy. A known water sample volume is filtered so that cells in the size range of the microorganisms of interest are captured. These are then stained and examined by microscopy. Typically, staining of specific microorganisms is obtained through use of immunofluorescent antibodies (IFAs). IFAs are fluorescent molecules chemically bonded to antibodies. The antibodies are produced to have binding specificity for particular target microorganisms or particular cell surface receptors. Hence, staining a target cell with an IFA specific for it causes the cell to fluoresce and "stand out" from background, unstained material when illuminated. Filters are examined under epifluorescence microscopy. When the organism(s) of interest are specifically stained, they fluoresce against the background. In order to retain organisms as small as bacteria, the filter used for capture must have a small pore size, typically 0.22–0.45 microns. The volume filtered is limited to several liters maximum as membranes quickly clog with particulates. Microscopic scanning for bacteria is labor intensive, requiring a trained microscopist and a large non-portable epifluorescence-equipped microscope.

Direct detection may also be accomplished using flow cytometry. Flow cytometry is a commonly used technique to measure the chemical or physical properties of cells. Cells flow by a measuring apparatus in single file while suspended in a fluid, usually air or water. In immunofluorescence flow cytometry, cells can be identified by attaching fluorescent antibodies to each cell:

- An antibody specific to the cell of interest is labeled with a fluorescent molecule or fluorochrome.
- The labeled antibody is mixed in solution with the cell of interest. The antibodies attach to specific sites on the cells (called antigens).
- The cells are passed in single file in a stream of liquid past a laser(s), which illuminates the fluorochromes and causes them to fluoresce at a different wavelength.
- A photomultiplier or photodiode is used to detect a burst of fluorescence emission each time a marked cell passes in front of the detector.
- The number of marked cells can then be counted. Antibodies can be chosen that are highly-specific to the cell(s) of interest.

Flow cytometry is currently used for a wide variety of applications including: measuring helper T-lymphocyte counts to monitor HIV treatment, measuring tumor cell DNA content in determining cancer treatment, and separating X- and Y-chromosome bearing sperm for animal breeding.

Figure 1:
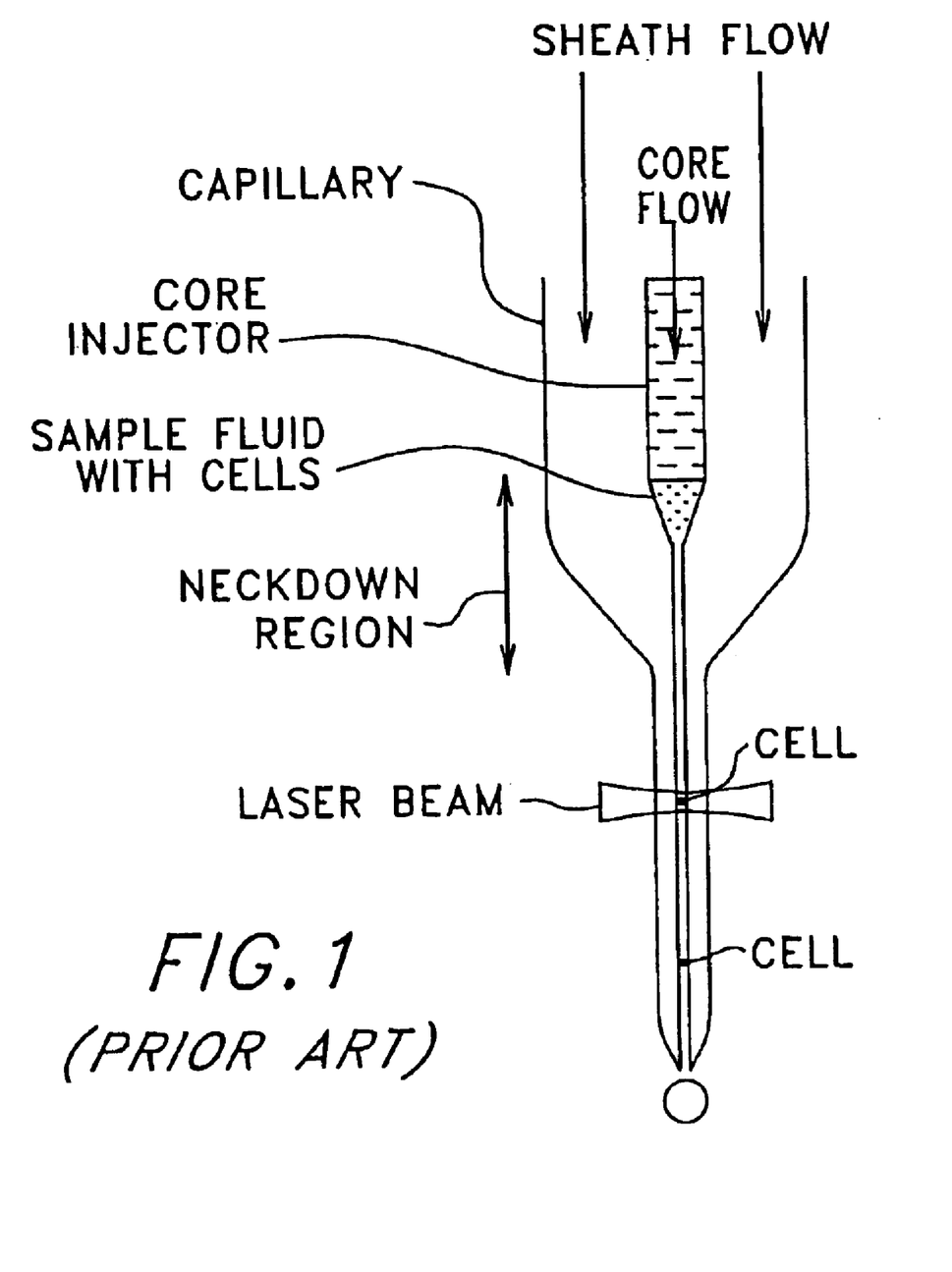
FIG. 1 (prior art) is a schematic drawing showing a conventional flow cytometry system.

FIG. 1 (prior art) shows a typical flow cytometry system (from Shapiro, Practical Flow Cytometry, 2nd Edition). Putting flow cytometry into practice involves using two concentric cylindrical streams of fluid. The inner flow or core flow contains the cells to be sampled. The purpose of the outer stream or sheath flow is to reduce the diameter of the core flow. As the core and sheath fluids reach the tapered region of the flow, the cross-sectional area of the core flow is reduced. A small bore core flow (~20 $\mu$m) allows for precision photometric measurements of cells in the flow, illuminated by a small diameter laser beam; all of the cells will pass through nearly the same part of the beam and will be equally illuminated. Why not just pass the cells through a small-bore transparent tube? Small diameter orifices are generally unworkable because they experience frequent clogging. All commercial flow cytometers now use a sheath/core flow arrangement.

Laser-induced fluorescence of fluorescent labels in a flow cytometer is a uniquely powerful method of making fast, reliable, and relatively unambiguous detections of specific microorganisms, such as foodborne pathogens. Several monographs describe the methods and applications of flow cytometry (e.g., Flow Cytometry: First Principles by A. L. Givan, 1992, and references therein). The successful detection of single cells relies on several critical factors. First, the laser power must be sufficient to generate a large enough number of fluorescence photons during the brief passage of the labeled microbial cell through the irradiated region. Specifically, it is essential that the number of photons generated be large enough so that the fluorescence burst can be reliably differentiated from random fluctuations in the number of background photons. Second, reducing the background is important, i.e., minimizing the number of unwanted photons that strike the detector which arise from scattering and fluorescence of the apparatus and of impurities and unbound dye in the flowing liquid.

Historically, flow cytometers have been very large, expensive laboratory-based instruments. They consume large amounts of power, and use complex electronics. They are not typically considered within the realm of portable devices. The size (desktop at the smallest), power requirements, and susceptibility to clogging (requiring operator intervention) of conventional flow cytometers precludes their use for many applications, such as field monitoring of water biocontamination.

A technique called solid-phase cytometry is more rapid than flow cytometry. In this method, the fluid matrix is concentrated and then filtered. Fluorescently labeled microorganisms are then imaged on a filter membrane with a laser scanning system, detected, and enumerated. Using fluorescently tagged antibodies, this technique can detect specific microorganisms, and is highly suited for low concentrations of microorganisms. However, the high cost of this system (>$100,000) makes its use problematic for many applications, especially those requiring continuous on-site monitoring.

U.S. Pat. No. 6,309,886, "High throughput analysis of samples in flowing liquid," by Ambrose et al. is an invention for the high throughput analysis of fluorescently labeled DNA in a transparent medium. This invention is a device that detects cells in a flow moving toward an imaging device. The flow is in a transparent tube illuminated in the focal plane from the side by a laser with a highly elongated beam. Although this invention does not suffer from the drawbacks listed above for alternative technologies, it is not suitable for applications where the flow medium is not transparent.

A need remains in the art for improved apparatus and methods for high throughput analysis of samples in a translucent flowing liquid.

SUMMARY OF THE INVENTION

The present invention has the advantages of solid-phase cytometry, including detection of individual microorganisms, at a much lower cost (<$10,000). This invention is based on taxonomic identification using fluorescent dyes, including immunofluorescent dyes. The detection steps include:

An antibody specific to the cell species of interest is labeled with a fluorescent molecule or fluorochrome.

The labeled antibody is mixed in solution with the cell species of interest. The antibodies attach to specific sites on the cells (antigens).

The cells are passed in a vertical stream of liquid toward a laser diode, gas laser, or the like, which illuminates the fluorochromes and causes them to fluoresce at a longer wavelength.

A low-cost CCD (charge coupled device) 2-D detector detects a flash of fluorescence emission each time a marked cell is illuminated by the laser diode while passing through the focal plane of the detector.

The number of marked cells is then counted via computer. Antibodies can be chosen that are highly specific to the cells of interest.

One object of the present invention is to provide apparatus and methods for high throughput, high sensitivity detection and identification of samples in a translucent or transparent flowing liquid. This object is accomplished by providing a relatively large cross section axial flow, in which cells or other target particles suspended in a liquid are observed as they emerge from a tube oriented generally along the optical axis of imaging optics.

The present invention includes apparatus and methods for imaging multiple fluorescent particles in a sample passing through a flow channel. A flow channel defines a flow direction for samples in a flow stream and has a viewing plane nearly perpendicular to the flow direction. A clear volume between the illuminated flow volume and the imaging optics is provided in some embodiments. A beam of illumination is formed as a column having a size that can effectively cover the viewing plane, and illuminates the flow nearly end on, or from the side. Imaging optics are arranged to view the focal plane to form an image of the multiple fluorescent sample particles in the flow stream. A camera records the image formed by the imaging optics.

In one embodiment, optics are provided for multiple emission wavelength dispersion, including a multi-segmented, motorized filter wheel.

The present invention includes apparatus and methods for for identifying particles in a sample of liquid flowing within a flow channel along a flow axis comprising a transparent element transverse to the flow axis for terminating the flow channel and diverting the sample, a waste conduit adjacent to the transparent element for discharging the sample, an illumination beam positioned to illuminate an illumination zone within the sample, and an imaging element for imaging a focal plane transverse to the flow axis within the illumination zone.

Generally the focal plane is spaced apart from the transparent element and a clear volume separates the transparent element and the imaging element.

The imaging element comprises a color filter, optics, and a CCD camera.

The waste conduit may comprise an opening formed in the flow channel, or a specially designed flow block. The flow block includes an input tube for providing the sample to the flow block, an output tube for discharging the sample from the flow block, and a flow path formed within the flow block and connected to the input tube and the output tube. The flow path passes adjacent to the transparent element, and the focal plane is located in the flow path before the sample passes adjacent to the transparent element.

The illumination may be provided by a laser or by an LED.

The invention may further include a multicolor detection assembly comprising a generally planar filter wheel located between the transparent element and the imaging element, the filter wheel plane tilted with respect to the optical axis of the imaging element, wherein the filter wheel includes at least two filter portions, each filter portion having a different thickness or index of refraction, and a filter wheel motor for rotating the filter wheel such that illumination from the illumination zone passes through each filter portion and is imaged by the imaging element during part of the integration time. Spaced apart images of each imaged particle are then formed for each filter portion.

In the case of detection of pathogenic microorganisms in ground beef, the resulting bacteria/extract mixture would contain, blood, fat, and tissue, and would likely be optically thick over circa 1 mm or greater distance necessitating a transparent gap (air or immersion liquid) between imaging optics and the focal plane of the instrument.

In this invention, as a microorganism passes up the delivery tube its spot size (the size that the image of the microorganism occupies on the CCD) decreases as it approaches the focal plane of the CCD camera; above the focal plane the spot size increases. The spot size reaches it minimum in the focal plane of the CCD fore-optics. In order to maximize the signal to noise ratio, the spot size must be minimized. This occurs when an exposure is made while the microorganism (or fluorescent target particle) is passing through the focal plane perpendicular to the optical axis of the CCD camera.

DETAILED DESCRIPTION OF THE PREFERRED EMBODIMENTS

Figure 2:
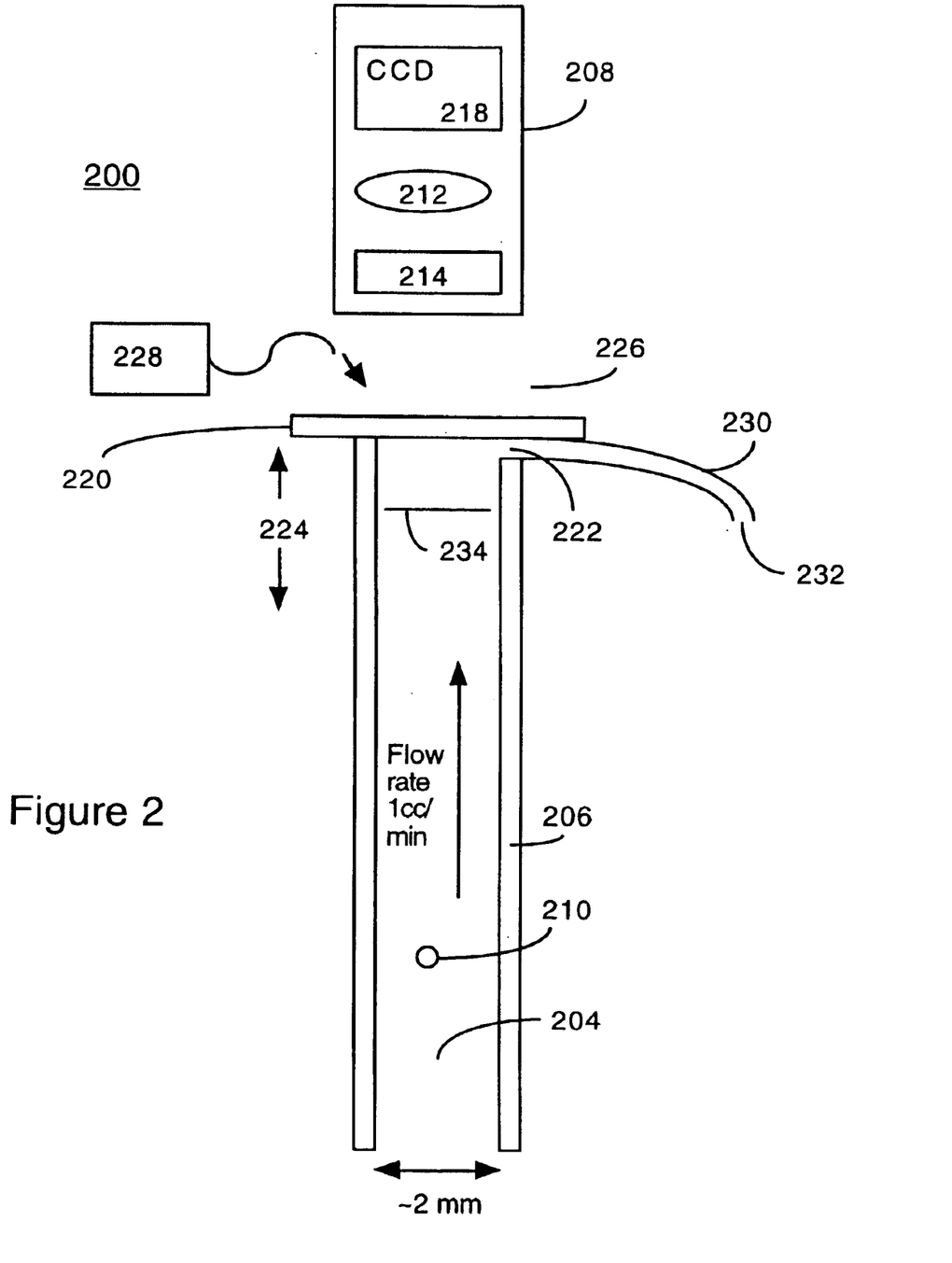
FIG. 2 is a simplified schematic drawing showing improved apparatus for detecting particles in a translucent flow according to the present invention.

FIG. 2 is a simplified schematic drawing showing improved apparatus 200 for detecting target particles in a translucent flow according to the present invention. It is not to scale, and is not the most efficient embodiment. However, it illustrates the operation of the present invention. The sample suspended in an aqueous solution 204 flows up tube 206 toward imaging assembly 208 such that sample particles 210 can be imaged at focal plane 234 onto a CCD camera 218 (or other camera, such as a digital CMOS camera) and then counted or measured photometrically by computer (not shown). The imaging assembly 208 includes focusing optics 212 and, with a single color instrument, a filter 214 isolating the wavelength(s) of fluorescent emission.

Normally the sample will flow upward, vertically. In the embodiment of FIG. 2, the sample would then flow out of a horizontal drain, a channel 222 under a glass cover slip 220, into waste output tube 230. In another, more preferred embodiment, a flow block 300 would channel the flow (see FIG. 3). Volume 226 is filled with air, or transparent liquid, in a preferred embodiment of the invention. This allows the illuminated volume 224 to be viewed without intervening solvent, decreasing the optical depth of the intervening fluid to near zero. The illuminated volume 224 is not required to be thin (i.e., it is not formed as a ribbon), nor does it have to be illuminated via laser. Illumination 228 via incoherent light, such as a light-emitting diode, is not only acceptable, but in some ways is preferable, as this minimizes effects of interference on increasing the non-uniformity of the illumination in the illuminated volume. In addition, illumination at an angle of circa 30 degrees to the optical axis is preferred as it avoids problems with relatively high intensity backscattering directly into the camera optics. Although some of this backscatter is eliminated by color filter 214, filters are not perfect and will transmit some backscatter outside their passbands. Backscattered light is also reduced by painting the interior of exit hole 302 flat black.

The column of sample 204 is both viewed and illuminated end-on. One method of doing this is with a dichroic mirror (not shown) allowing both the viewing path and illumination path to coincide with the flow axis, but in the opposite direction, similar to the optics in an epifluorescent microscope. The volume imaged is controlled by the depth of focus of the imaging optics, and is normally kept small to prevent the negative effects of foreshortening on the resulting digital images. The ideal situation is where a particle flowing up the flow tube is imaged in the same pixel(s).

Figures 3A, 3B, 3C:
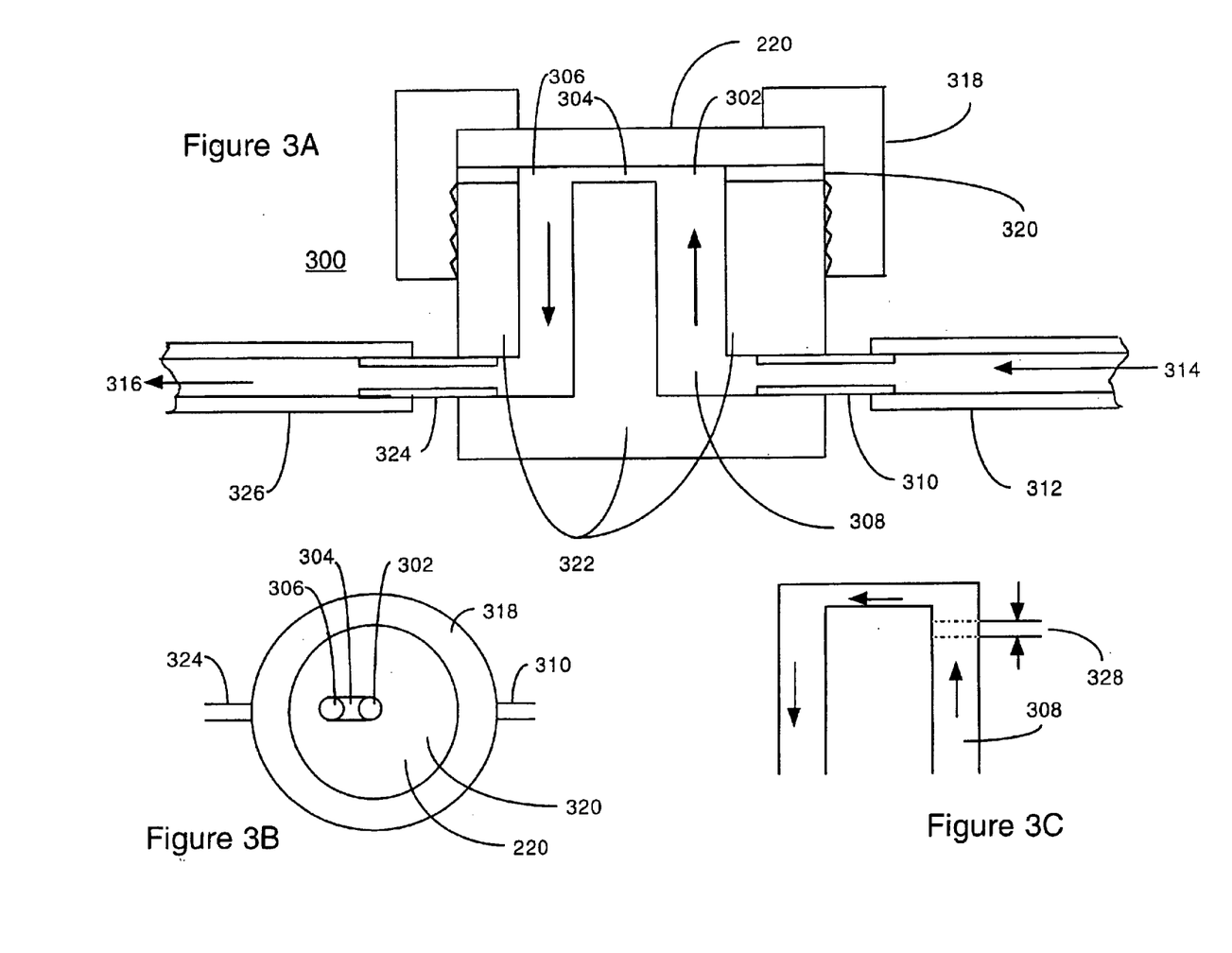
FIG. 3 is an isometric drawing of a flow block used in the apparatus of FIG. 2.

As a particle 210 to be imaged passes up tube 206, its spot size (the size that the image of the microorganism occupies on CCD 218) decreases as it approaches the focal plane 234 of the CCD camera, reaches its minimum in the focal plane of the CCD fore-optics 212, and increases again above the focal plane. FIGS. 3C and 6 show this process in more detail.

The cross-section of the flow tube that can be conveniently imaged is not dependent on the opacity of the sample fluid and can be very large (say a square of dimension 3 mm×3 mm) allowing an extremely high flow throughput of sample. It is expected that flow throughputs of greater than 1 ml/minute can be achieved in a straightforward way. It is expected that the flow velocity will be low enough to be laminar.

Because of slower flow of particles near the walls of the tube, particles near the walls may appear in multiple images and this effect preferably is taken into account when calibrating the device. Calibration can be effected by using samples of calibrated fluorescent beads of uniform intensity.

This invention, when combined with the use of fluorescent antibodies to selectively tag microorganisms, allows the detection of pathogenic microorganisms in food and water, just to name two applications. For example, *E. coli* O157:H7 is detected in a buffer solution extracted from ground beef. High-resolution images allow determination of the size of the fluorescently-tagged particles, allowing for screening based on size determination. It is possible to perform detection, enumeration, and size screening in real time.

Another issue is the large contribution from unbound dye in a transparent fluid, which contributes to the detected background and can contribute in large measure to background noise, even when it originates well outside focal plane 234. It contributes to the detected signal to a depth on the order of 1 optical depth, which becomes quite large as a medium approaches being transparent. This effect has less of an impact on translucent media. There are two ways of reducing the background from unbound dye:

1) Washing

Microorganisms are separated from the fluid after they have been labeled with dye. This can be done via centrifugation and/or filtering. Unbound dye is washed from the microorganisms with one or more resuspension and separation steps. The microbes are then resuspended in fluid. The detection step is performed on the washed and resuspended microbes.

2) Using a DNA-Enabled Dye

A method that is simpler than washing involves using a dye that is rendered fluorescent only after it has been attached to DNA. Unbound dye would not fluoresce. An example is the TOTO dye.

FIGS. 3A–3C illustrate a preferred embodiment of a flow block 300 used in the apparatus of FIG. 2. The embodiment of FIGS. 3A–3C is one specific example of a flow block. FIG. 3A is a side cutaway view, FIG. 3B is a top plan view, and FIG. 3C is a side view illustrating the depth of focus within the flow.

Input flow 314 enters aluminum flow block 300 via input tube 312 and connecting tube 310. Input tube 312 is typically formed of Tygon or the like. Connecting tube 310 is epoxied to flow block 300. Input flow 314 enters flow path 308 formed by walls 322, traveling upward, then to the left, and finally back down to exit 316 via tubes 324 and 326.

Transparent window 220 is connected to flow block 300 by brass screw-on cap 318. A teflon gasket 320 provides the seal between flow block 300 and window 220. Flow 314 appears at window 220 via exit hole 302, passes under window 220 while in channel 304, and leaves window 220 at waste receptacle hole 306. This is shown more clearly in FIG. 3B.

FIG. 3B is a top view of flow block 300. Entrance connecting tube 310 provides input flow 314 to flow block 300. Flow block walls 322 are partially obscured by gasket 320, but exit hole 302, channel 304 and waste hole 306 are visible through window 220. Waste flow 316 exits at connecting tube 324.

FIG. 3C illustrates depth of focus 328 within flow path 308. The focal plane of CCD 218 is located within illuminated zone 224, below flow channel 304.

Figure 4:
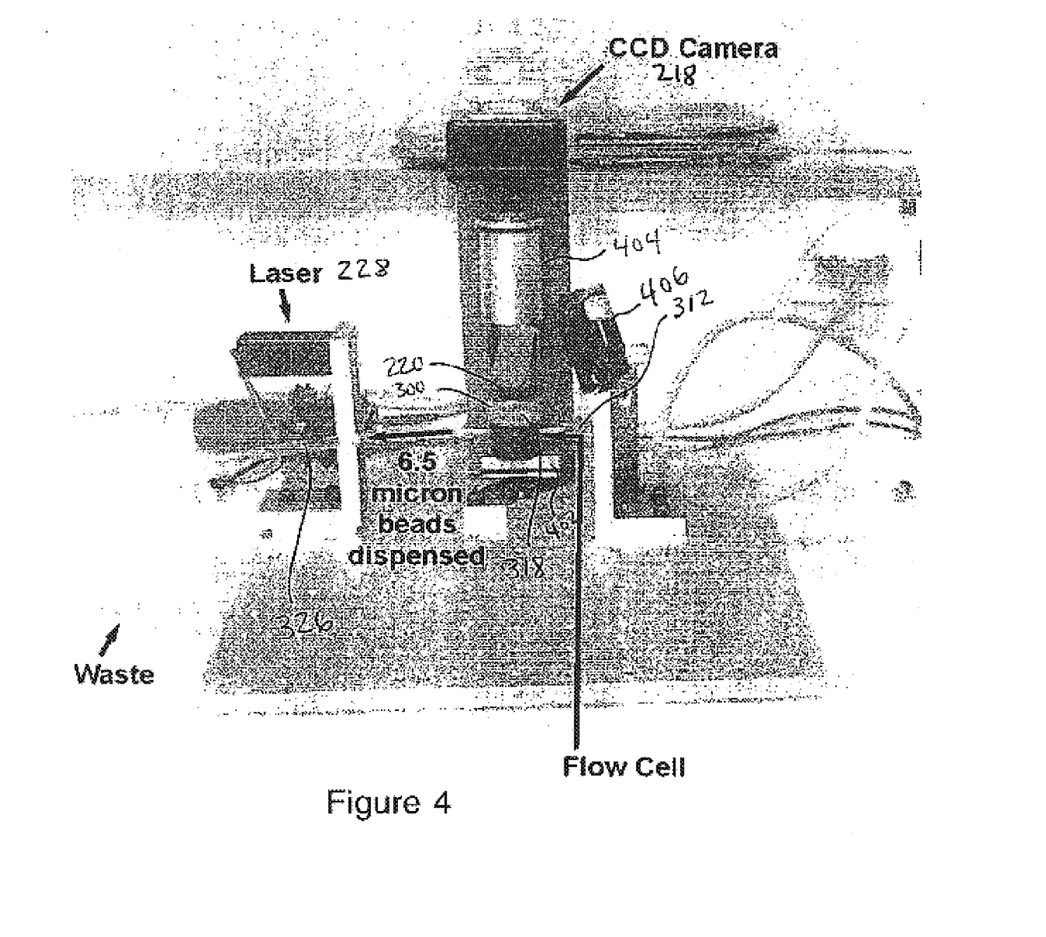
FIG. 4 is an isometric drawing of one embodiment of the particle detecting apparatus of FIG. 2.

FIG. 4 is an isometric drawing of one specific example of the particle detecting apparatus of FIG. 2. Aluminum flow block 300 of FIG. 3 is shown here mounted on mount 402. Glass cover slip 220 constrains the liquid flow out of exit hole 302 in flow block 300. CCD camera 218 (black, upper portion of figure) is mounted vertically and connected to fore-optics 212 (shown in FIG. 2) with an aluminum mounting tube 404. Sample or fluorescent calibration beads are pumped into flow block 300 via tube 312 with a syringe pump (not shown).

Figure 5A:
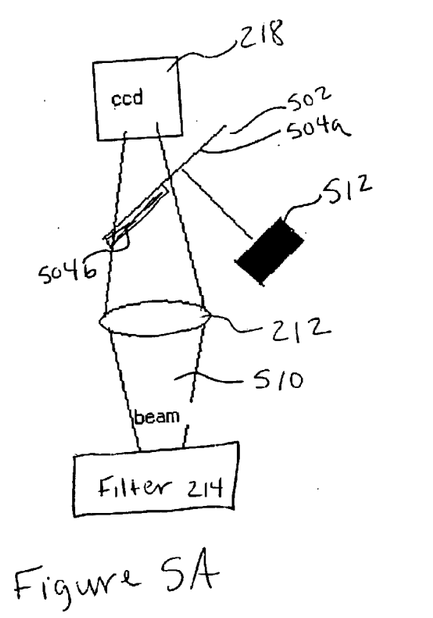
FIG. 5 is a schematic drawing showing the use of a filter wheel arrangement for multicolor detection.
Figure 5B:
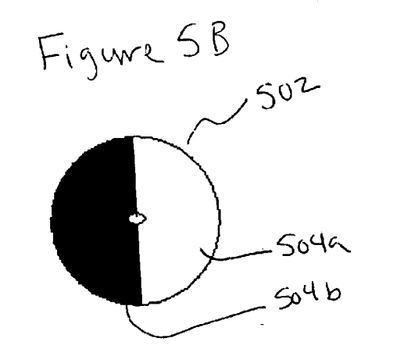
Figure 5C:
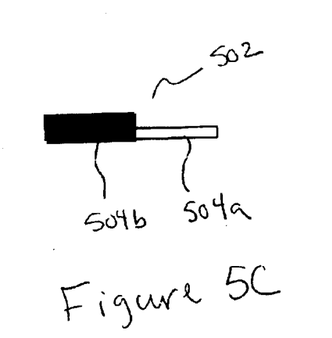
Figure 5D:
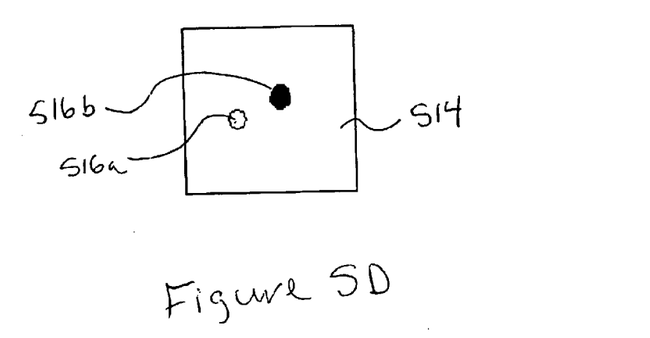

The mouth of exit hole 302 is illuminated with a laser 228. The laser beam is steered into exit hole 302 by mirror 406. Exit tube 326 removes the sample after imaging FIGS. 5A through 5D illustrate the use of a filter wheel arrangement for multicolor detection. Two-color emission is illustrated in FIGS. 5A–5D, but three or more colors may be detected by using more than two filter portions 504a 504b, etc. FIG. 5A is a simplified schematic diagram showing the use of filter wheel 502 in the particle detecting apparatus of FIG. 2. FIGS. 5B and 5C show filter wheel 502 from one side and from an end, respectively. FIG. 5D shows an image of one particle detected at CCD 218.

FIG. 5A illustrates how multicolor detection is accomplished. The basic premise for the filter wheel system is that multicolor light emission 510 from illuminated portion 224 of flow tube 206 is sent through tilted filter wheel 502, which is rotating. As filter wheel 502 rotates it alternates between passing emission from a first emission wavelength and a second emission wavelength through the system onto CCD 218.

When a beam of light passes through tilted filter portions 504 the beam is displaced by an amount that depends on the index of refraction and the thickness of each filter portion. Filter portions 504 are designed to have slightly different thicknesses/indices, creating a multiple image for each bacterium or other imaged particle, one image for each emission color.

A schematic diagram of the filter wheel system is shown in FIG. 5A. The system is composed of imaging optics 212, stand alone filter 214, filter portions 504 mounted in rotating filter wheel 502, and a motor 512 to rotate filter wheel 502. The light 510 emitted from illuminated particles 210 in flow tube 206 first passes through filter 214, which blocks wavelength of the illuminating light 228. The remaining beam then passes through imaging optics 212, shown as a single lens FIG. 5A, but generally comprising two or more achromatic lenses. The beam narrows as it approaches CCD 218 and then passes through tilted filter wheel 502. Filter wheel 502 rotates very rapidly compared to the integration (exposure) time, so that beam 510 is incident on each filter portion for (typically) half of the integration time. The two slightly displaced, colored beams then focus onto CCD 218, forming spots 516 in image 514 as shown in FIG. 5D. The filter segment sizes can be adjusted to compensate for the difference in intensity at each wavelength.

The angle and thicknesses of filter portions 504 in filter wheel 502 are selected to produce the best image quality and displacement between the two beams. In terms of image quality, the tilt of the filter introduces astigmatism into the image. If the tilt angle is too large, the astigmatism will be unacceptable. If the tilt angle is too small, however, the differential displacement of beams can only be achieved with vastly different thicknesses for the two filters, which leads to the two beams not focusing within a common focal plane. From trials, and for the filters chosen, an angle of roughly 20 degrees works well, with central spot sizes roughly 25 microns across, surrounded by a broader, very diffuse ring.

Once the tilt of filter wheel 502 is set, the displacement is controlled by the thicknesses of filter positions 504. To simplify the image analysis, the displacement between the two beams is preferably large enough to clearly separate the two spots but still small enough to clearly associate the two spots from each color with each other. The ideal separation is between about 10 and 20 pixels.

Those skilled in the art of optics and optical filter design will appreciate that the exact thicknesses of the filter portions 504 to achieve this separation depends on the index of refraction of filter portions 504 and will need to be adjusted depending on the final filter selection. Increasing the thickness of a filter 504 can easily be accomplished by optically cementing clear glass to the filter. The direction of the spot displacement can easily be adjusted by rotating flow tube 206 and CCD 218 relative to filter wheel 502 tilt angle. Since the CCD pixels are generally not square (e.g. in our experiments 8.5 microns by 19.75 microns), the offset between the spots in pixels can be adjusted by aligning the direction of displacement with the short side, the long side, or an angle in between.

Multicolor detection of three or more colors can easily be implemented with the invention. A motorized filter wheel 502 containing multiple filter segments 504 (one to select each wavelength of multiple emission wavelengths) is inserted so that each segment will pass through beam 510 before striking the CCD 218 (or other imaging detector). Filter motor 512 is driven at a high rotation rate so that the time of rotation is much faster than the time it takes a particle to move in the image or across the focal plane. The filters are of differing index of refraction and/or thickness, so that the image of a particle on the detector will move (chop) significantly and in a direction and distance on the detector that can be calibrated. The detection of multiple spots on the detector with an appropriate distance and direction of separation can then be taken as a detection in one or more wavelength bands.

Multicolor detection makes it possible to use more than one fluorescent label for redundancy or to detect multiple parameters. For example, one label could be a fluorescently labeled antibody specific to the microorganism of interest, another could be a viability label. The two together would test specifically for live organisms of interest. A multicolor system could excite labels at one or more wavelengths (using multiple LEDs or lasers) and would provide for detection at multiple emission wavelengths.

An alternative multicolor embodiment would use a prism (not shown) between fore-optics 212 and CCD 218 to disperse the light from individual target particles into low-resolution spectra on the surface of the CCD. Another alternative embodiment would use a transmission grating (not shown) between fore-optics 212 and CCD 218 to disperse light from target particles.

Figure 6A:
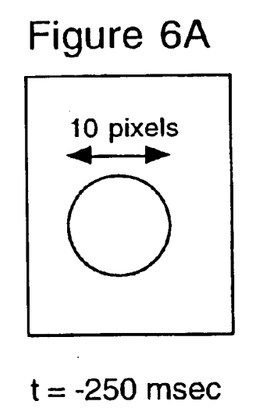
FIG. 6 is a diagram illustrating the spot size of a detected particle before, at, and after the focal plane or the present invention.
Figure 6B:
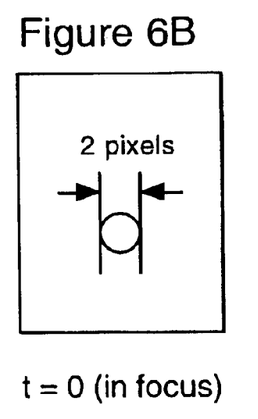
Figure 6C:
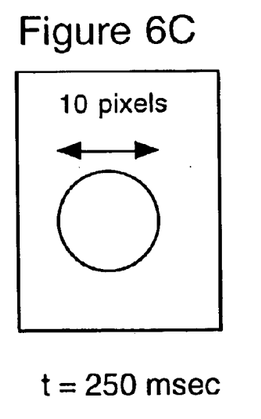

FIG. 6 is a diagram illustrating the spot size of a detected particle before, at, and after the focal plane or the present invention. In this invention, as a microorganism 210 passes up delivery tube 206 its spot size (the size that the image of the microorganism occupies on the CCD 218) decreases as it approaches the focal plane 234 of the CCD camera. See FIG. 6A. Above the focal plane the spot size increases again. See FIG. 6C. The spot size reaches it minimum in the focal plane of the CCD fore-optics 212, as shown in FIG. 3B. In the example of FIGS. 6A–C, the spot size at CCD 18 is about 10 pixels across 250 msec before the particle reaches the focal plane. The spot size reaches its minimum, about 2 pixels across, as the particle passes through the focal plane. About 250 msec after the particle passes through the focal plane, the spot size has increased to on the order of 10 pixels across again.

Noise in the detection comes from extraneous material in the flow (esp. any unbound dye, that is dye not attached to microorganisms of interest) called background noise, as well as noise from the CCD (including thermal noise and CCD pixel readout noise). Signal is measured only over those pixels from which a contribution is made from a fluorescing microorganism. Noise increases (both from the CCD and background) with the number of pixels over which a detection is made. Therefore, the highest signal to noise (S/N) measurement will be made from an exposure during which the measured microorganism was closest to the focal plane.

In order to maximize signal to noise ratio, the spot size needs to be minimized, preferably to just a few pixels. This happens when an exposure is made while the microorganism is passing through the focal plane perpendicular to the optical axis of the CCD camera. This vertical passage minimizes streaking of microorganism images onto numerous CCD pixels, which occurs when a microorganism has a large transverse velocity across the CCD frame.

There is an optimum depth of focal plane 234 below the surface of flow column 206. If the focal plane of the invention is too close to the surface of the flow column, the transverse velocity of fluid produced by fluid exiting the flow column (channel) will produce streaking and lower the S/N of a detection. If the focal plane of the invention is too far from the surface of the flow column, S/N is lowered due to the absorption and scattering of illumination and emission of light within the flow column. We have had success with an empirically determined focal depth of about 200 microns below the top of the flow column.

What is claimed is:

1. Apparatus for identifying particles in a sample of liquid flowing within a flow channel along a flow axis comprising:
   a transparent element transverse to the flow axle for terminating the flow channel and diverting the sample;
   a waste conduit adjacent to the transparent element for discharging the sample;
   an illumination beam positioned to illuminate, through the transparent element, an illumination zone within the sample; and
   an imaging element for imaging a focal plans transverse to the flow axis within the illumination zone.

2. The apparatus of claim 1 wherein the focal plane is spaced apart from the transparent element.

3. The apparatus of claim 2, further including a clear volume separating the transparent element and the imaging element.

4. The apparatus of claim 1 wherein the imaging element comprises a color filter, optics, and a CCD camera.

5. The apparatus of claim 1, wherein the waste conduit comprises an opening formed in the flow channel.

6. The apparatus of claim 1, wherein the waste conduit comprises a flow block including:
   an input tube for providing the sample to the flow block;
   an output tube for discharging the sample from the flow block;
   a flow path formed within the flow block and connected to the input tubs and the output tube;
   wherein the flow path passes adjacent to the transparent element; and
   wherein the focal plane is located in the flow path before the sample passes adjacent to the transparent element.

7. The apparatus of claim 1 wherein the illumination is provided by a laser.

8. The apparatus of claim 1 wherein the illumination is provided by an LED.

9. The apparatus of claim 1, further comprising multicolor detection assembly comprising:
   a generally planar filter wheel located between the transparent element and the imaging element, the filter wheel plane tilted with respect to the optical axis of the imaging element, wherein the filler wheel includes at least two filter portions, each filter portion having a different thickness or index of refraction;
   a filter wheel motor for rotating the filter wheel such that illumination from the illumination zone passes through each filter portion and is imaged by the imaging element during part of the integration time;
   wherein spaced apart images of each imaged particle is formed for each filter portion.

10. Apparatus for identifying partial in a sample of liquid flowing within a flow channel along a flow axis comprising:
    a transparent element transverse to the flow axis for terminating the flow channel and diverting the sample;
    a waste conduit adjacent to the transparent element for discharging the sample; wherein the waste conduit comprises a flow block including:
    an input tube for providing the sample to the flow block;
    an output tube for discharging the sample from the flow block;
    a flow path formed within the flow block and connected between the input tube and the output tube;
    wherein the flow path passes adjacent to the transparent element;
    an illumination beam positioned to illuminate, through the transparent element, an illumination zone within the flow path; and
    an imaging element for imaging a local plane transverse to the flow axis within the illumination zone.

11. The apparatus of claim 10, further comprising multicolor detection assembly comprising:
    a generally planar filter wheel located between the transparent element and the imaging element, the filter wheel plane tilted with respect to the optical axis of the imaging element, wherein the filter wheel includes it least two filter portions, each filter portion having a different thickness or index of refraction;
    a lifter wheel motor for rotating the filter wheel such that illumination from the illumination zone passes through each filter portion and is imaged by the imaging element during part of the integration time;
    wherein spaced apart images of each imaged particle is formed for each filter portion.

12. A method for identifying particles in a sample of liquid flowing within a flow channel along a flow axis comprising the steps of:
    terminating the flow channel and diverting the sample transverse to the flow axle;

illuminating, generally along the flow axis, an illumination zone within the sample; and imaging a focal plane transverse to the flow axis within the illumination zone.

13. The method of claim 12 wherein the imaging step comprises the steps of:

color filtering the illumination;

focussing the filtered illumination, and imaging the focussed, filtered illumination with a CCD camera.

14. The method of claim 12 further comprising the steps of:

sequentially applying filter portions to the illumination, while tilting the filter portions with respect to the optical axis of the illumination wherein each filter portion has a different thickness or index of refraction; and forming spaced apart images of each imaged particle for each filter portion.

\* \* \* \* \*

UNITED STATES PATENT AND TRADEMARK OFFICE
CERTIFICATE OF CORRECTION

PATENT NO.    : 6,765,656 B2
DATED         : July 20, 2004
INVENTOR(S)   : Paul E. Johnson It is certified that error appears in the above-identified patent and that said Letters Patent is hereby corrected as shown below:

Column 1,
Line 34, delete "Microbiological" and insert -- Molecular microbiological --;

Column 4,
Line 50, delete "distance" with -- distance, --;

Column 7,
Line 19, delete "beanis" and insert -- beam is --;
Line 20, insert period at end of sentence;
Lines 27-28, delete "one side and from an end" and insert -- an end and from one side --;
Line 51, delete "wavelength" and insert -- the wavelengths --;
Line 54, delete "lens FIG. 5A" and insert -- lens in FIG. 5A --;

Column 8,
Line 51 delete "interest" and insert -- interest, and --;
Line 65, delete "or" and insert -- of --

Column 9,
Line 4, delete "it" and insert -- its --;
Line 5, delete "3B" and insert -- 6B --;
Line 33, delete "206" and insert -- 204 --;
Line 54, delete "plans" and insert -- plane --;

Column 10,
Line 4, delete "tubs" and insert -- tube --;
Line 26, delete "is" and insert -- are --;
Line 28, delete "partial" and insert -- particles --;
Line 46, delete "local" and insert -- focal --;

UNITED STATES PATENT AND TRADEMARK OFFICE
CERTIFICATE OF CORRECTION

PATENT NO. : 6,765,656 B2
DATED : July 20, 2004
INVENTOR(S) : Paul E. Johnson It is certified that error appears in the above-identified patent and that said Letters Patent is hereby corrected as shown below:

Column 10 (cont'd),
Line 53, delete "it" and insert -- at --;
Line 56, delete "lifter" and insert -- filter --;
Line 67, delete "axle" and insert -- axis --;

Signed and Sealed this

Thirtieth Day of November, 2004

JON W. DUDAS
*Director of the United States Patent and Trademark Office*